United States Patent
Sakanishi

(10) Patent No.: US 6,401,916 B2
(45) Date of Patent: Jun. 11, 2002

(54) SOFT INTRAOCULAR LENS CONTAINER HAVING FOLDING FUNCTION

(75) Inventor: Kotaro Sakanishi, Aichi (JP)

(73) Assignee: Menicon Co., Ltd., Nagoya (JP)

( * ) Notice: Subject to any disclaimer, the term of this patent is extended or adjusted under 35 U.S.C. 154(b) by 1 day.

(21) Appl. No.: 09/730,776

(22) Filed: Dec. 7, 2000

(30) Foreign Application Priority Data

Dec. 9, 1999 (JP) ............................................. 11-350545

(51) Int. Cl.[7] .............................................. A45C 11/04
(52) U.S. Cl. ........................................ 206/5.1; 206/438
(58) Field of Search ...................... 206/5.1, 438; 606/1, 606/107; 623/6

(56) References Cited

U.S. PATENT DOCUMENTS

| | | | |
|---|---|---|---|
| 4,736,836 A | * | 4/1988 | Alongi et al. ................ 206/438 |
| 5,100,410 A | | 3/1992 | Dulebohn |
| 5,139,501 A | | 8/1992 | Klaas |
| 5,171,241 A | | 12/1992 | Buboltz et al. |
| 5,199,559 A | * | 4/1993 | Dark ........................... 206/438 |
| 5,281,227 A | | 1/1994 | Sussman |
| 5,290,293 A | | 3/1994 | Van Noy et al. |
| 5,454,818 A | | 10/1995 | Hambleton et al. |
| 5,702,400 A | | 12/1997 | Brown et al. |
| 6,183,513 B1 | * | 2/2001 | Guenthner et al. ......... 206/316.1 |

* cited by examiner

Primary Examiner—David T. Fidei
(74) Attorney, Agent, or Firm—Oblon, Spivak, McClelland, Maier & Neustadt, P.C.

(57) ABSTRACT

A soft intraocular lens container having a folding function comprises a base plate 1 having a groove 2, a lens receiving mechanism formed in the base plate 1 and a cover wherein the lens receiving mechanism comprises a pair of holding portions 4, each formed at each side portion of the groove 2, which are adapted to receive haptics h of a soft intraocular lens, and clamping portions 6, each formed on each of the holding portions 4, which clamp an optical portion o of the soft intraocular lens having the haptics h to be put on said holding portions 4, and wherein the base plate 1 is capable of folding the optical portion o of the soft intraocular lens held between said clamping portions 6 into two when both sides of the base plate 1 are clamped so that the base plate is pressed toward the groove 2, and the cover has a plurality of bayonet pawls projecting toward a rear surface side of the cover, the bayonet pawls being capable of engaging with bayonet openings formed in the base plate 1 at both side portions with respect to the groove 2 whereby the cover covers the soft intraocular lens received in the lens receiving mechanism and is fixed to the both side portions of the base plate 1.

5 Claims, 9 Drawing Sheets

F I G. 1 (a)
F I G. 1 (b)
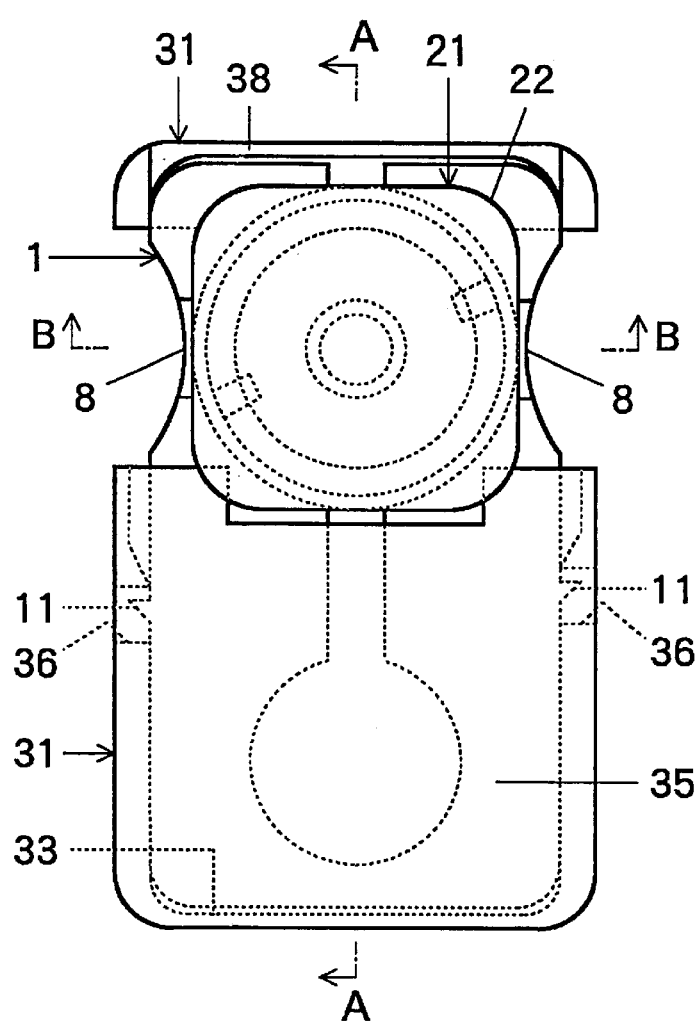
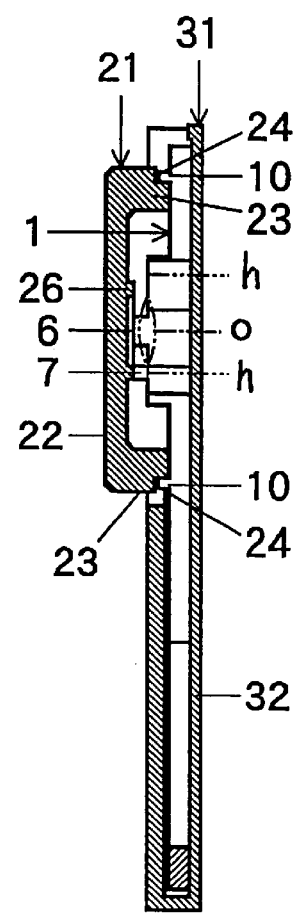
F I G. 1 (c)
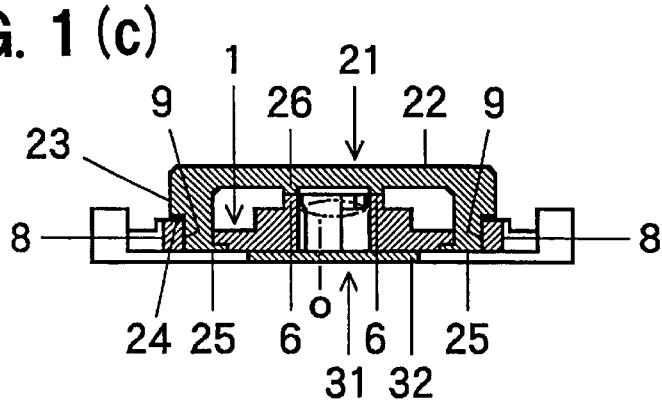

F I G. 3 (a)
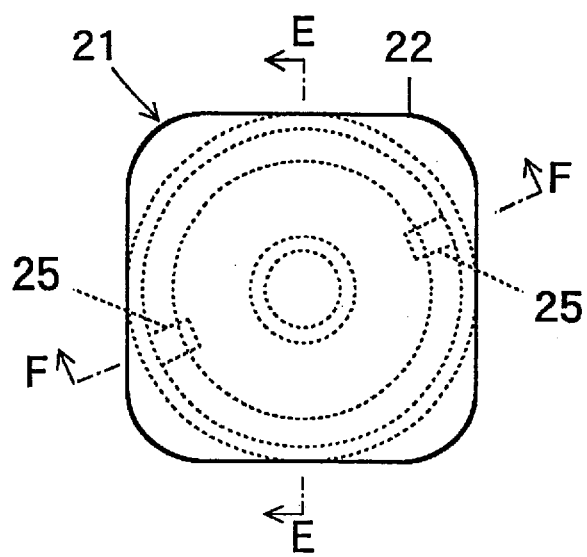
F I G. 3 (b)
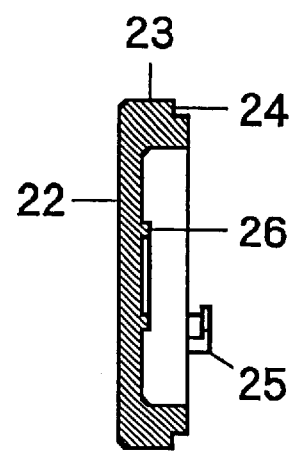
F I G. 3 (c)
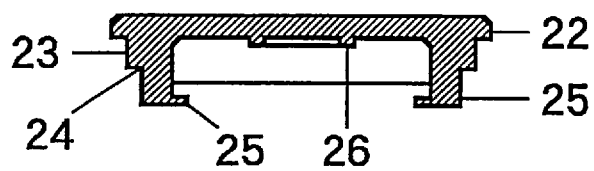
F I G. 3 (d)
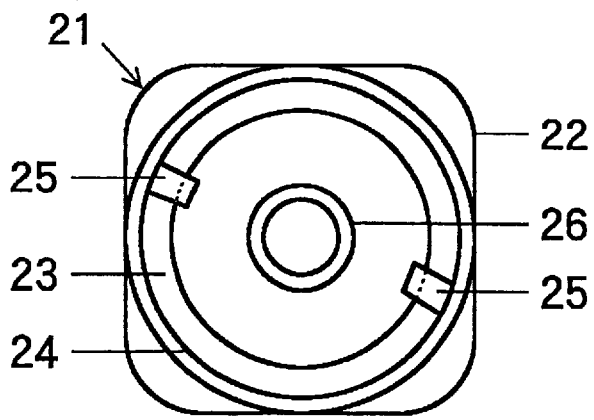

FIG. 5(a)
FIG. 5(b)
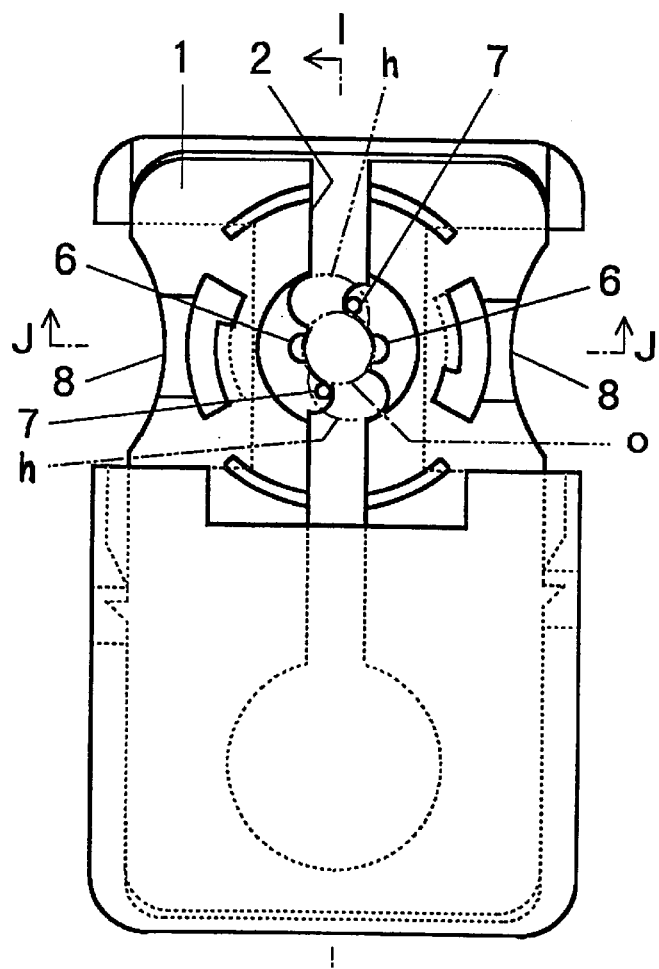
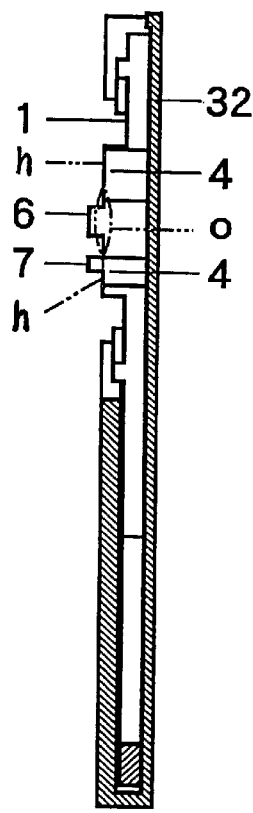
FIG. 5(c)
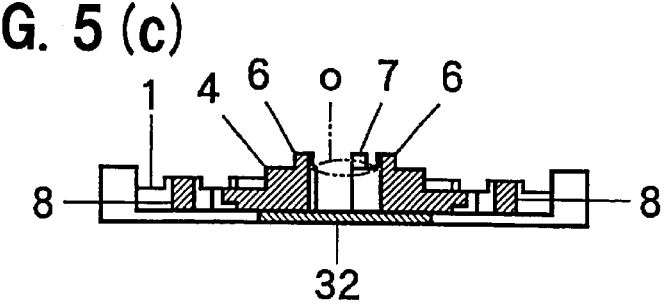

F I G. 8 (a)
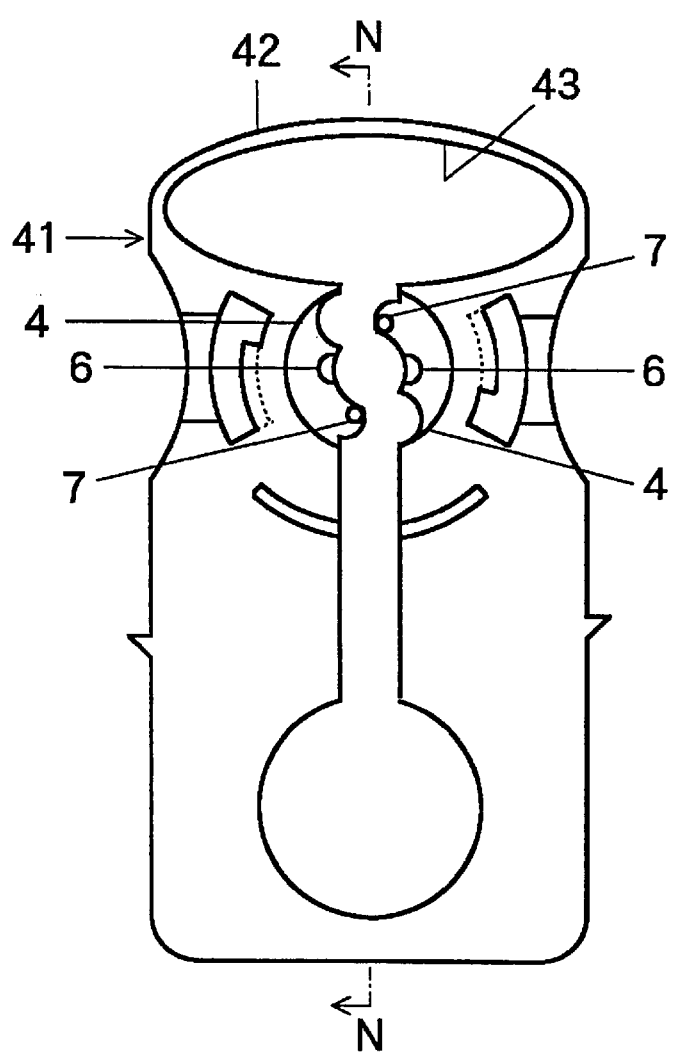
F I G. 8 (b)
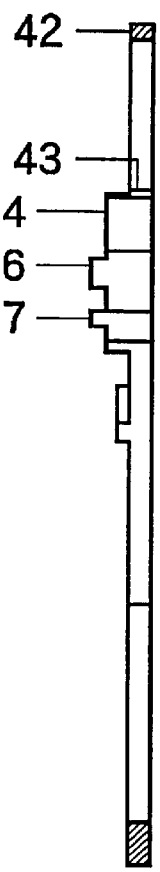

SOFT INTRAOCULAR LENS CONTAINER HAVING FOLDING FUNCTION

BACKGROUND OF THE INVENTION

1. Field of the Invention

The present invention relates to a container for receiving a soft intraocular lens capable of being folded. In particular, the present invention relates to a container having a function of folding the soft intraocular lens received therein.

2. Discussion of Background

An intraocular lens comprises an optical portion of a circular lens and two curved flexible haptics, wherein each one end of the curved flexible haptics is bonded to the periphery of the circular lens at opposing positions and each other end of them is extended to opposite sides of the optical portion. The optical portion of the soft intraocular lens is elastic so as to be folded unlike the optical portion of a hard intraocular lens.

If a person feel uncomfortable in the crystal lens of his or her eye due to cataract, normally it is extracted surgically; a circular opening is formed in a front portion of the crystal lens capsule after conducting corneal or corneoscleral incision; the cataract is removed through the circular opening and an intraocular lens is inserted in remained capsular bag through the incision instead of the crystal lens. In this case, the corneal or corneoscleral incision should be small as possible in order to minimize surgical intervention to the patient. The intraocular lens usually used is a soft intraocular lens having an optical portion which can be folded. When the soft intraocular lens is inserted into the crystal lens capsule, it is passed through a circular opening of the crystal lens capsule in a state that the intraocular lens is folded into two, whereby the size is reduced. The soft intraocular lens inserted into the capsule restores itself the shape from the two-folded state to the original state, i.e., the state before being folded, due to the elasticity of the optical portion.

1) First Conventional Case

The soft intraocular lens is sold or stored in a state that it is received in a container of synthetic resin and is sterilized together with the container wherein the container is packed with an additional wrapping.

When the soft intraocular lens is used, the additional wrapping is opened to expose the sterilized container, and the cover of the container is removed. Then, the intraocular lens in the container is picked up by forceps to take it out from the container. The optical portion of the soft intraocular lens is folded into two with forceps for bending or a bending tool. The soft intraocular lens folded into two is picked with forceps for inserting and it is inserted in the state of being folded into the crystal lens capsule through a corneal or corneoscleral small incision.

2) Second Conventional Case

A lens case for receiving a soft intraocular lens was proposed, which functions to fold the soft intraocular lens in the lens case along an optical folding line.

The proposed lens case comprises a rigid base, an IOL folder and a cap, as disclosed in U.S. Pat. 5,281,227.

The rigid base comprises a thin plate portion and an annular projection formed on an upper face of the thin plate portion wherein the positions of the haptics of the soft intraocular lens are determined on an upper face of the peripheral wall of the annular projection. The soft intraocular lens having the haptics whose positions are determined on the annular projection, is prevented from rotation with respect to the rigid base.

The IOL folder is so constructed that a pair of jaws are formed so as to oppose to each other in an inner face of both long side portions of an elongated circular frame; ledges are formed at lower edges of the pair of jaws, and the optical portion of the soft intraocular lens is inserted between the pair of jaws so that the lens portion of the optical portion is placed on the pair of ledges. The soft intraocular lens whose optical portion is placed on the pair of ledges is rotatable with respect to the IOL folder.

The IOL folder is put on the thin plate portion of the rigid base so that the pair of jaws of the IOL folder are inserted into a central opening of the annular projection of the rigid base. The annular projection of the rigid base is inserted between the both long side portions of the IOL folder. Projections formed in outer faces of both short side portions of the IOL folder are inserted into grooves formed in side edges of the thin plate portion of the rigid base. With such construction, the IOL folder can be attached to or detached from the rigid base.

The position of the soft intraocular lens is determined in such a manner that the optical portion of the lens is inserted between the pair of jaws of the IOL folder to be placed on the pair of ledges, and the haptics are placed on the annular projection of the rigid base. After the IOL folder has been detached from the rigid base and when the both long side portions of the IOL folder are clamped, a space between the pair of jaws is narrowed whereby the optical portion of the soft intraocular lens is clamped and fixed. When a clamping force to the both long side portions is increased, the optical portion of the soft intraocular lens is folded into two along a diameter, as a folding line, which is parallel to the long side portions.

When the IOL folder is attached to the rigid base, the angle formed between a longitudinal direction of the IOL folder and a longitudinal direction of the rigid base can be selected to be 90° or 0° (or any desired angle). In cases of the angle being 90° and 0°, the direction of the folding line of the optical portion of the soft intraocular lens differs 90°.

The cap having a circular cover plate of circular shape has bayonet pawls which are formed at symmetric positions in a lower face of the circular cover plate and are projected therefrom.

The cap is put on the IOL folder on the rigid base in such a manner that the soft intraocular lens placed on the ledges in a central portion of the IOL folder and the annular projection of the rigid base is covered with the circular cover plate of the cap, and the bayonet pawls of the cap engage with bayonet openings formed in the thin plate portion of the rigid base respectively. Thus, the IOL folder is fixed to the rigid base by means of the cap.

In the first conventional case, the soft intraocular lens is picked up with the forceps for taking out from the container and is handled to the forceps for inserting via the forceps for folding or the folding tool. Accordingly, some steps of handling was required and much time and labor were required for the handling. Further, there is a high possibility that the soft intraocular lens may be contaminated, damaged or dropped during the handling. In addition, the forceps for taking out and the forceps for folding are costly.

In the second conventional case, the following steps are taken when the soft intraocular lens received in the lens case is to be folded. Namely, (1) the cap is removed from the rigid base, (2) the both long side portions of the IOL folder are clamped to pick the optical portion of the soft intraocular lens, (3) the IOL folder is removed from the rigid base and (4) the clamping force to the IOL folder is increased to fold the optical portion of the intraocular lens. Accordingly, many operations and much labor were required in order to fold the soft intraocular lens received in the lens case.

In the second conventional case, since the lens case has such structure that the optical portion of the soft intraocular lens is inserted between the pair of jaws of the IOL folder to place the optical portion on the ledges, and the haptics of the intraocular lens are placed on the annular projection of the rigid base at a lower side of the IOL folder, the position of the optical portion which is pressed and folded is at a deep position in a space between the pair of jaws of the IOL folder. Accordingly, the forceps for taking out has to be lowered to a deep position in a narrowed space within the jaws of the IOL folder in order to pick the optical portion held between the jaws. Thus, the picking operation to the folded optical portion of the soft intraocular lens is not easy.

Further, since the optical portion of the soft intraocular lens is placed on the ledges of the IOL folder with its lens surface downward, the lens surface of the optical portion may stick to the ledges when the optical portion, which is usually made of an elastic synthetic resin, is sticky. In this case, when the optical portion tacked to the ledges is taken from the ledges, traces of the ledges may remain in the optical portion.

SUMMARY OF THE INVENTION

It is an object of the present invention to provide a soft intraocular lens container having a folding function to a soft intraocular lens, which allows easy operations for taking the soft intraocular lens folded into two from the container and which prevents a lens surface of the optical portion of the soft intraocular lens from contacting the structural elements of the container.

In accordance with a first aspect of the present invention, there is provided a soft intraocular lens container having a folding function which comprises a base plate having a groove, a lens receiving mechanism formed in the base plate, said lens receiving mechanism comprising a pair of holding portions, each formed at each side portion of the groove, which are adapted to receive haptics of a soft intraocular lens, and clamping portions, each formed on each of the holding portions, which clamp an optical portion of the soft intraocular lens having said haptics to be put on said holding portions, wherein the base plate is capable of folding the optical portion of the soft intraocular lens held between the clamping portions into two when both sides of the base plate are clamped so that the base plate is pressed toward the groove, and a cover having a plurality of bayonet pawls projecting toward a rear surface side of the cover, said bayonet pawls being capable of engaging with bayonet openings formed in the base plate at both side portions with respect to the groove whereby the cover covers the soft intraocular lens received in the lens receiving mechanism and is fixed to the both side portions of the base plate.

In a second aspect of the present invention, there is provided the soft intraocular lens container according to the first aspect, wherein the lens receiving mechanism is adapted to raise the optical portion of the soft intraocular lens from a space between the clamping portions when the optical portion is folded into two.

According to a third aspect of the present invention, there is provided the soft intraocular lens container according to the first aspect, wherein the lens receiving mechanism is adapted so that a lens surface of the optical portion does not contact the lens receiving mechanism when the soft intraocular lens is received in the lens receiving mechanism.

According to a fourth aspect of the present invention, there is provided the soft intraocular lens container according to the first aspect, wherein the container further comprises a preventive means for displacement, which prevents any of the clamping portions from shifting in a direction of the thickness of the base plate when the both sides of the base plate are clamped so that the base plate is pressed toward the groove.

According to a fifth aspect of the present invention, there is provided the soft intraocular lens container according to the fourth aspect, wherein the preventive means for displacement has a guide plate extending along a rear surface of the base plate, and the guide plate is provided at its base end side with an insertion portion for receiving a base end side of the base plate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows the soft intraocular lens container having a folding function according to a first embodiment of the present invention wherein FIG. 1(a) is a plan view, FIG. 1(b) is a cross-sectional view taken along a line A—A in FIG. 1(a) and FIG. 1(c) is a cross-sectional view taken along a line B—B in FIG. 1(a);

FIG. 2 shows a base plate in the soft intraocular lens container wherein

FIG. 3 shows a cover in the soft intraocular lens container wherein FIG. 3(a) is a plan view, FIG. 3(b) is a cross-sectional view taken along a line E—E in FIG. 3(a), FIG. 3(c) is a cross-sectional view taken along a line F—F in FIG. 3(a) and FIG. 3(d) is a bottom view;

FIG. 4 shows a preventive means for displacement in the soft intraocular lens container wherein

FIG. 5 shows a state that the cover is removed from the soft intraocular lens container wherein FIG. 5(a) is a plan view, FIG. 5(b) is a cross-sectional view taken along a line I—I in FIG. 5(a) and FIG. 5(c) is a cross-sectional view taken along a line J—J in FIG. 5(a);

FIG. 6 shows a state that a soft intraocular lens is folded in the soft intraocular lens container wherein

FIG. 7 shows a base plate in the soft intraocular lens container having a folding function according to a second embodiment of the present invention wherein

FIG. 8 shows a base plate in the soft intraocular lens container having a folding function according to a third embodiment of the present invention wherein FIG. 8(a) is a plan view and FIG. 8(b) is a cross-sectional view taken along a line N—N in FIG. 8(a)

DETAILED DESCRIPTION OF THE PREFERRED EMBODIMENTS

Figure 2A:
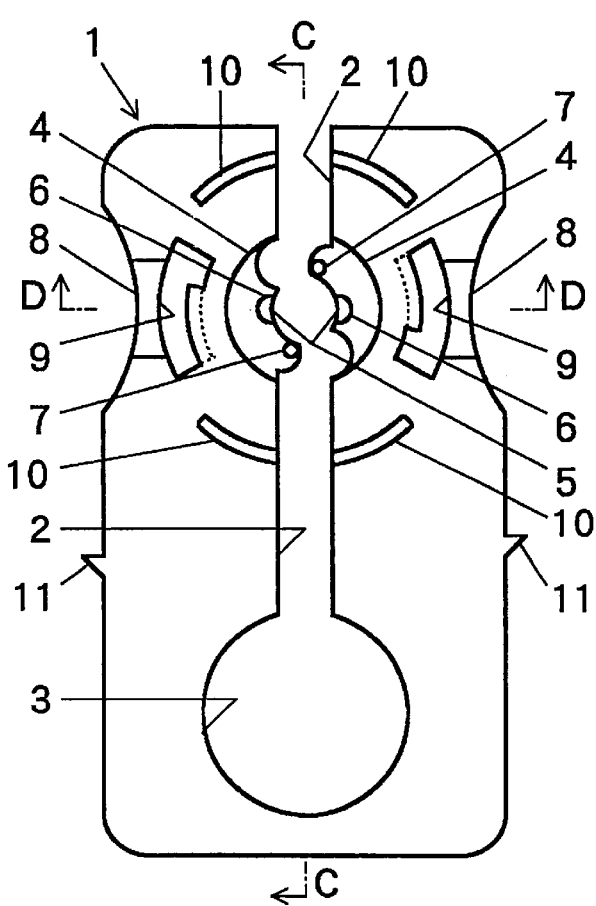
FIG. 2(a) is a plan view.

Preferred embodiments of the soft intraocular lens container having a folding function according to the present invention will be described with reference to the drawings wherein the same reference numerals designate the same or corresponding parts.

A first embodiment of the soft intraocular lens container will be described with reference to FIGS. 1 to 6.

The soft intraocular lens container having a folding function comprises a base plate 1, a cover 21 and a preventive means for displacement 31 as shown in FIG. 1. These structural components are respectively molded products of synthetic resin such as polypropylene, polyvinyl chloride, polyethylene, polybutadiene or polystyrene.

Figure 2B:
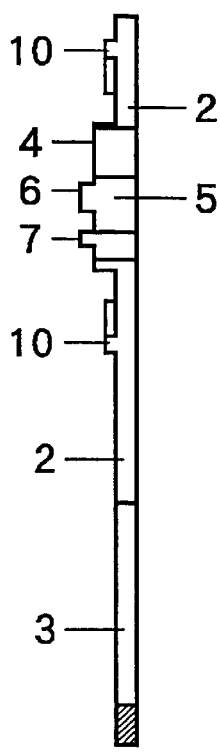
FIG. 2(b) is a cross-sectional view taken along a line C—C in FIG. 2(a)
Figure 2C:
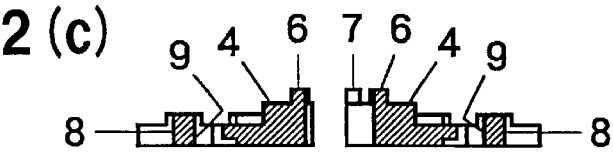
FIG. 2(c) is a cross-sectional view taken along a line D—D in FIG. 2(a) and FIG. 2(d) is a plan view partly omitted.

The base plate 1 is a rectangular plate having round corner portions as shown in FIG. 2(a) to FIG. 2(c). The base plate 1 has a groove 2 extended from a top end (i.e., an upper end side in FIG. 2(a)) of the rectangular base plate 1 toward the base end side (i.e., a lower end side in the same figure) of the base plate 1 so that the top end side of the groove 2 is opened at a central portion in a shorter side of the rectangular base plate 1 and the base end side of the groove 2 is communicated with a circular opening 3 formed at the base end area of the base plate 1.

In both side portions of an upper surface area of the base plate 1 (i.e., a left side portion and a right side portion of the base plate 1 with respect to the groove 2 in the plan view of FIG. 2(a)), holding portions 4 each having an arch-like shape are formed projecting in an island-like shape so as to oppose to each other with respect to the groove 2. Arch-like outer peripheries of the opposing holding portions 4 define parts a circle having a diameter which is slightly larger than the entire length of a soft intraocular lens including haptics, i.e., haptics received in the soft intraocular lens container. The height of the opposing holding portions 4 is flush with each other.

An arch-like recess 5 is formed in a central portion of each of the holding portions 4 of the base plate 1, which oppose symmetrically with respect to a point on a line extending longitudinally in the groove 2. A pair of clamping portions 6 are formed in upper surfaces of the opposing holding portions 4 so as to be adjacent to the arch-like recesses 5 respectively. Inner side surfaces of the clamping portions 6 which oppose to each other with respect to the groove 2 and inner surfaces of the recesses 5 which also oppose to each other with respect to the groove 2 define parts of a cylindrical surface having a diameter slightly larger than the diameter of the optical portion of the soft intraocular lens. In other words, inner surfaces of the holding portions 4 formed in the base plate 1 which are at symmetric positions with respect to the groove 2 and the pair of clamping portions 6 define a circular opening having a diameter slightly larger than the diameter of the optical portion of the soft intraocular lens received in the container.

The height of the pair of clamping portions 6 is flush with each other and is substantially the same as the thickness of the optical portion of the soft intraocular lens.

The holding portion 4 having an island-like shape formed at a left side of the base plate 1 (in a plan view of FIG. 2(a)) has an arch-like recess 5 at a top end side of the base plate 1 in a portion facing the groove 2 (i.e., a right side of the holding portion 4), an archlike projection at a base end side of the base plate 1 in a portion facing the groove 2 (i.e., a right side of the holding portion 4), and a pin to prevent lens rotation 7 formed in an upper surface of the projection, i.e., the holding portion 4. The holding portion 4 having an island-like shape formed at a right side of the base plate 1 (in a plan view of FIG. 2(a)) has an arch-like recess 5 at a base end side of the base plate 1 in a portion facing the groove 2 (i.e., a left side of the holding portion 4), an arch-like projection at a top end side of the base plate 1 in a portion facing the groove 2 (i.e., a left side of the holding portion 4), and a pin to prevent lens rotation 7 formed in an upper surface of the projection, i.e., the holding portion 4. Each of the pins to prevent lens rotation 7 formed in an upper surface of the left and right holding portions 4 has the same height as that of the clamping portions 6.

Figure 2D:
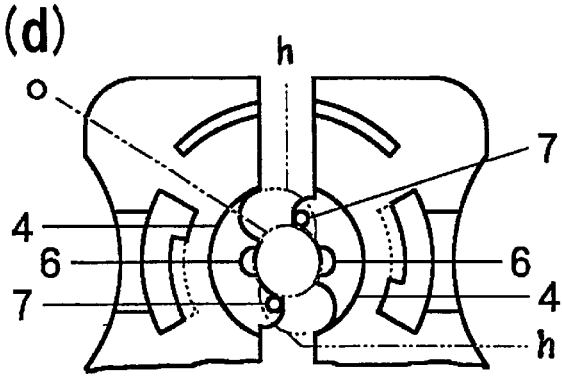

As shown in FIG. 2(d), the soft intraocular lens is inserted so that the optical portion o is placed in a space between the opposing clamping portions 6 and both of the haptics h are placed on the upper surface of the opposing holding portions 4 by passing respectively each of the haptics h between corresponding clamping portion 6 and corresponding pins to prevent lens rotation 7 of the corresponding holding portion 4. Then, the position of the soft intraocular lens is determined and is prevented from rotation around the center of the lens. The base plate 1 is provided with a lens receiving mechanism 4–7 at a top end side so that the soft intraocular lens is placed between the opposing clamping portions whereby the position is determined.

The lens receiving mechanism 4–7 has a structure that a lens surface of the optical portion o of the soft intraocular lens received therein does not contact structural components of the lens receiving mechanism. Accordingly, even when the optical portion o has some stickiness, the lens surface of the optical portion o does not stick to the lens receiving mechanism.

The base plate 1 is provided with a pair of gently curved arch-like recesses in outer side portions of the base plate 1 with respect to the groove 2 (i.e., a left side portion and a right side portion with respect to the groove 2 in the plan view of FIG. 2(a)) which are outside the holding portions 4. At positions adjacent to the recesses in outer surfaces of base plate 1, a pair of projections are formed as grasping portions 8. When the pair of grasping portions 8 are grasped and a grasping force is increased, the left side portion and the right side portion of the base plate 1 with respect to the groove 2 are deflected toward the groove 2 to bring them close to each other. When the grasping force is decreased, the left side portion and the right side portion of the base plate 1 move away due to their elasticity to return to the original position.

In each side portion of the base plate 1 with respect to the groove 2 at a position inside the grasping portion 8, a sector-like bayonet opening 9 is formed, the bayonet opening functioning to engage with the cover 21. Guiding projections 10 having an arch-like shape, which are for guiding the rotation of the cover 21, are formed at the top end side and the base end side of the base plate 1 with respect to the holding portions 4. A cylindrical surface defined by outer peripheries of the bayonet openings 9 formed in the left and right side portions of the base plate 1, inner peripheries of the guiding projections 10 formed at left and right sides with respect to the groove 2 and at the front and back of the holding portions 4, and inner peripheries of the grasping portions 8 as projections formed in the left and right side portions of the base plate 1, has the same axial center as a cylindrical surface defined by inner side walls of the clamping portions 6 and the surfaces of the recesses 5. The height of the guiding projections 10 and the height of the grasping portions 8 are flush with each other, but lower than the height of the holding portions 4.

Raised portions 11 are formed in outer side surfaces of the left and right side portions of the base plate 1 at a base end side of the base plate 1, the raised portion 11 functioning to engage with preventive means for displacement 31.

As shown in FIG. 3, the cover 21 comprises a square cover plate 22 having round corner portions wherein an annular peripheral wall 23 is concentrically formed in a rear surface of the cover plate 22; an annular groove 24 is formed in a lower corner portion of an outer periphery of the annular wall 23 so that the guiding projections 10 of the base plate 1 are fitted thereto, bayonet pawls 25 project from a lower surface of the annular wall 23 at symmetrical positions with respect to the center of the annular wall 23, the bayonet pawls 25 being engaged with the bayonet opening 9 of the base plate 1, and an annular projection 26 is formed concentrically in the rear surface of the cover plate 22 so that the annular projection 26 is in contact with or close to an upper surface of the clamping portions 6 and the pins to prevent lens rotation 7 formed in the base plate 1.

Figure 4A:
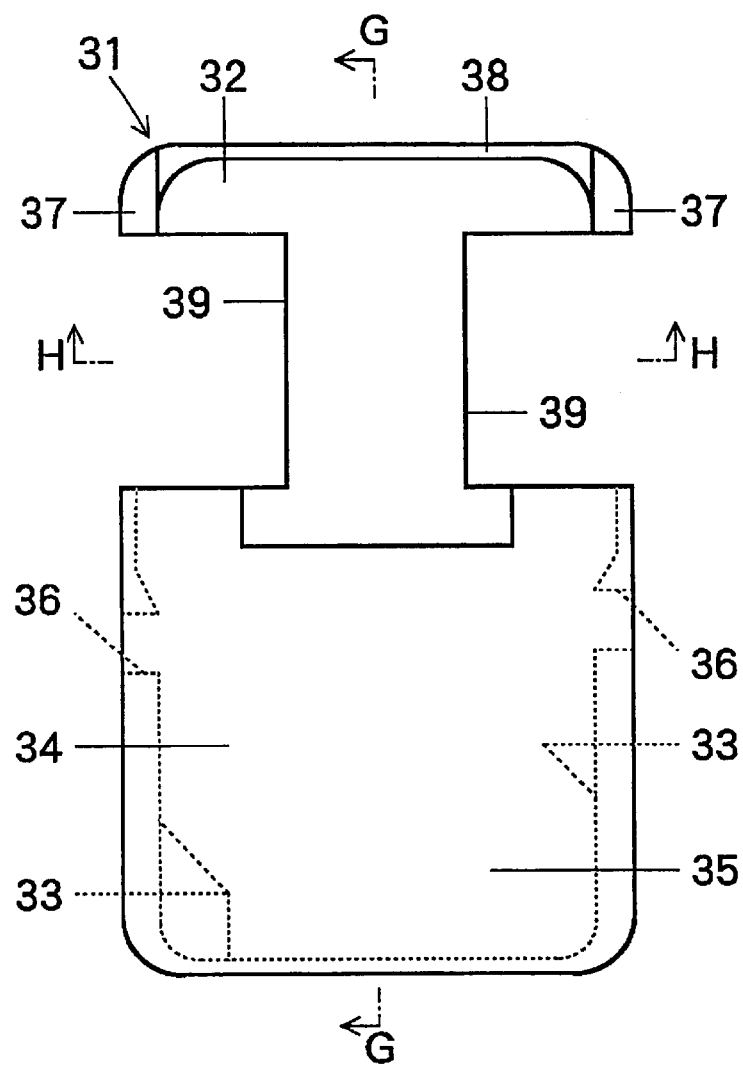
FIG. 4(a) is a plan view.
Figure 4B:
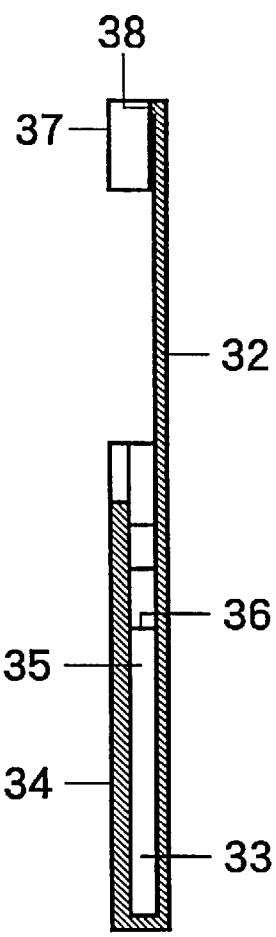
FIG. 4(b) is a cross-sectional view taken along a line G—G in FIG. 4(a) and FIG. 4(c) is a cross-sectional view taken along a line H—H in FIG. 4(a)
Figure 4C:
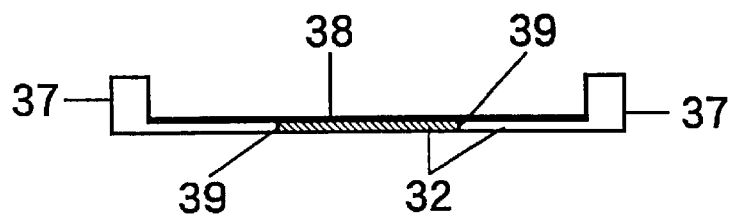

As shown in FIG. 4, the preventive means for displacement 31 comprises a guide plate 32 which is attachable to a rear surface of the base plate 1 wherein an upper plate 34 is formed in a portion facing the base plate 1 at a base end side, by interposing walls 33 formed at the base end side and both outer side edges, whereby a thin box-like receiving portion 35 is formed to allow the insertion of the base end portion of the base plate 1. Further, an engaging opening 36 is formed in each of the walls formed at both outer side edges of the base plate 1 so that each of the raised portions 11 formed at both outer side surfaces of the base plate 1 can be inserted.

A pair of short side walls 37 are formed at symmetrical positions in outer side portions of an top end side of an upper surface of the guide plate 32. A lower projection 38, to which the top end of the base plate 1 hits, is formed between the pair of short side walls 37 formed in the upper surface of the guide plate 32. Rectangular notched portions 39, which can receive fingers to grasp the grasping portions 8 formed in the base plate 1, are formed at symmetric positions between the side walls 37 and the receiving portion 35 of the guide plate 32.

The soft intraocular lens container according to this embodiment is so constructed that as shown in FIG. 1, the base end portion of the base plate 1 is inserted into the receiving portion 35 of the preventive means for displacement 31; the raised portions 11 formed in the outer surfaces of longer sides of the base plate 1 are inserted into the engaging openings 36 formed in the both side walls forming the receiving portion 35 of the preventive means for displacement 31; a lower surface of the base plate 1 is overlaid on an upper surface of the guide plate 32 of the preventive means for displacement 31; the pair of grasping portions 8 of the base plate 1 are made correspondence to the pair of notched portions 39 of the preventive means for displacement 31, and the base plate 1 is slightly movable in a direction of the groove 2 between the lower projection 38 formed at the top end of the preventive means for displacement 31 and the base end wall 33 of the receiving portion 35.

The cover 21 is fitted to the lens receiving mechanism 4–7, in which the soft intraocular lens are received as mentioned before, of the base plate 1 inserted in the preventive means for displacement 31. Namely, the cover plate 22 of the cover 21 is put on the lens receiving mechanism 4–7 to fit the annular groove 24 formed in the annular wall 23 of the cover 21 to the guiding projections 10 and projections at the grasping portions 8 in the base plate 1. Then, the annular projection 26 of the cover 21 is brought to contact or made close to upper surfaces of the pair of clamping portions 6 and the pins to prevent lens rotation 7 of the base plate 1. On the other hand, the bayonet pawls 25 of the cover 21 are inserted respectively into the bayonet openings 9 of the base plate through their widely opened portions, and the cover 21 is rotated slightly in a direction that the bayonet pawls 25 of the cover 21 are respectively engaged with narrow portions of the bayonet openings 9 of the base plate 1. Thus, the cover 21 covers the soft intraocular lens and fixes both side portions of the base plate 1 with respect to the groove 2.

Figure 6A:
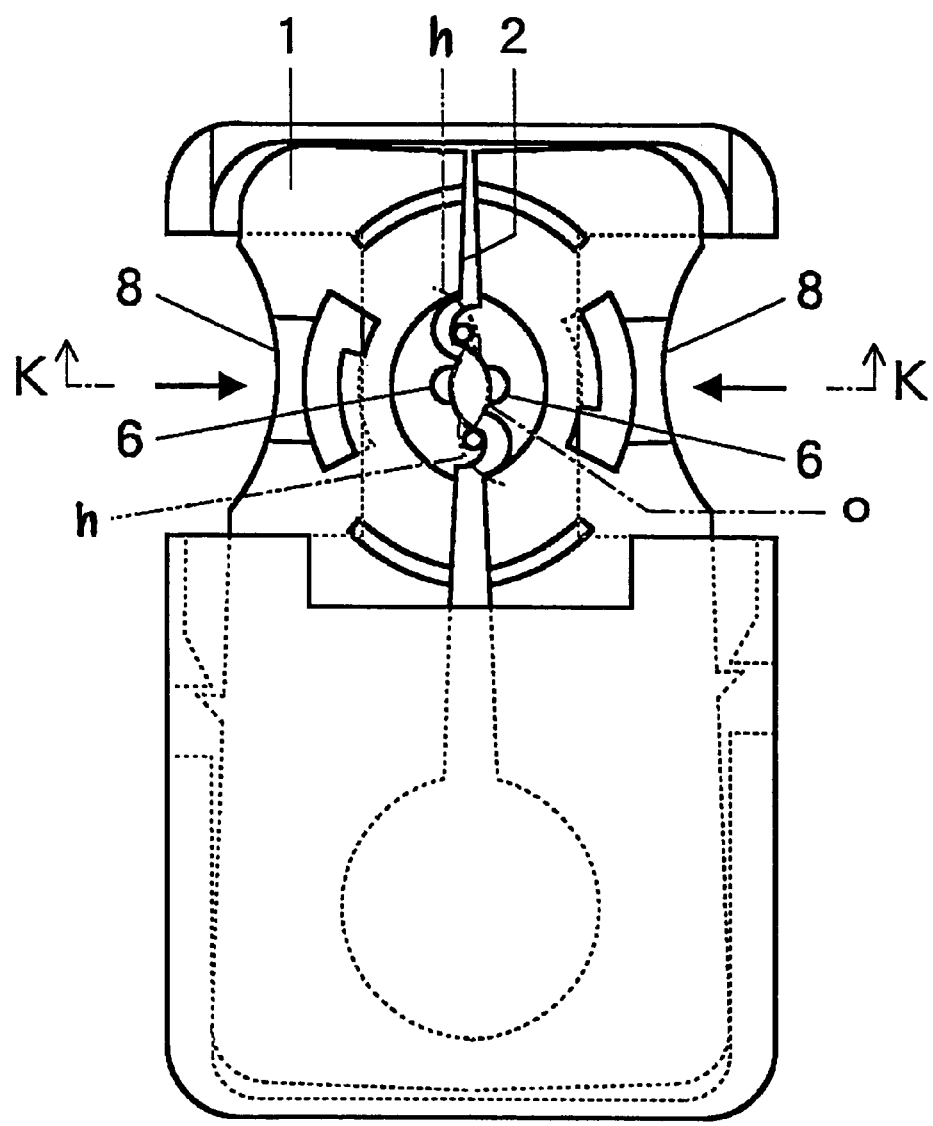
FIG. 6(a) is a plan view and FIG. 6(b) is a cross-sectional view taken along a line K—K in FIG. 6(a)
Figure 6B:
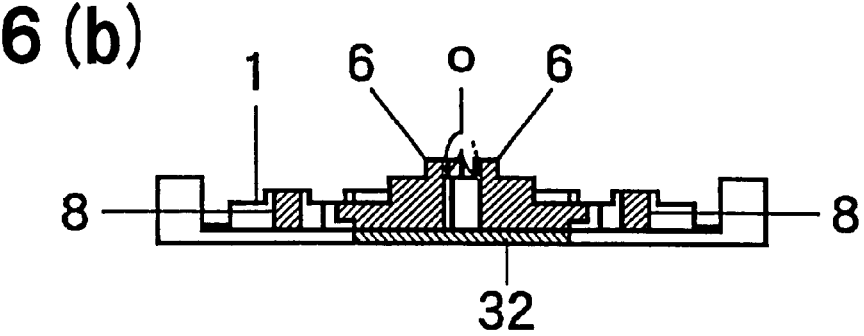

Explanation will be made as to how to fold the soft intraocular lens received in the container according to this embodiment. The container is held with a hand, and the cover 21 is rotated slightly with the other hand in a direction opposite to the direction of fitting to thereby remove the cover 21 from the base plate 1 as shown in FIG. 5. Then, the pair of grasping portions 8 of the base plate 1 are grasped with the thumb and the index finger of the hand holding the container. As a result, the left side portion and the right side portion of the base plate 1 with respect to the groove 2 are deflected toward the center of the groove 2 to approach each other along the flat surface of the guide plate 32 of the preventive means for displacement 31. Then, the optical portion o of the soft intraocular lens clamped between the pair of clamping portions 6 is folded into two along a folding line which is the diameter along a longitudinal direction of the groove 2, and the two-folded optical portion is projected upward from the clamping portions 6 as shown in FIG. 6.

The folding operations for the soft intraocular lens received in the container are performed at only two steps: an operation for removing the cover 21 and an operation for grasping the grasping portions 8 of the base plate 1. Thus, much labor is not required.

The two-folded soft intraocular lens is picked up, keeping a folding state, with forceps for inserting held by the hand which has removed the cover 21, and the two-folded soft intraocular lens is inserted with the forceps for inserting into the crystal lens capsule of an eye through an incision.

The operation for picking the two-folded soft intraocular lens with the forceps for inserting is easy since the soft intraocular lens is projected upward between the pair of clamping portions 6.

A second embodiment of the soft intraocular lens container will be described with reference to FIG. 7.

The soft intraocular lens container having a folding function of the second embodiment is the same as that in the first embodiment except that the lens receiving mechanism 4–7 of the base plate 1 is modified.

The lens receiving mechanism in the second embodiment comprises a pair of holding portions 4 formed in the base plate 1 in the same manner as the first embodiment provided that the height of clamping portions 6 and the height of pins to prevent lens rotation 7 which are formed in an upper surface of the respective holding portions 4 are flush with each other so that each of the holding portions 4 provides a flat mound portion 16.

Figure 7A:
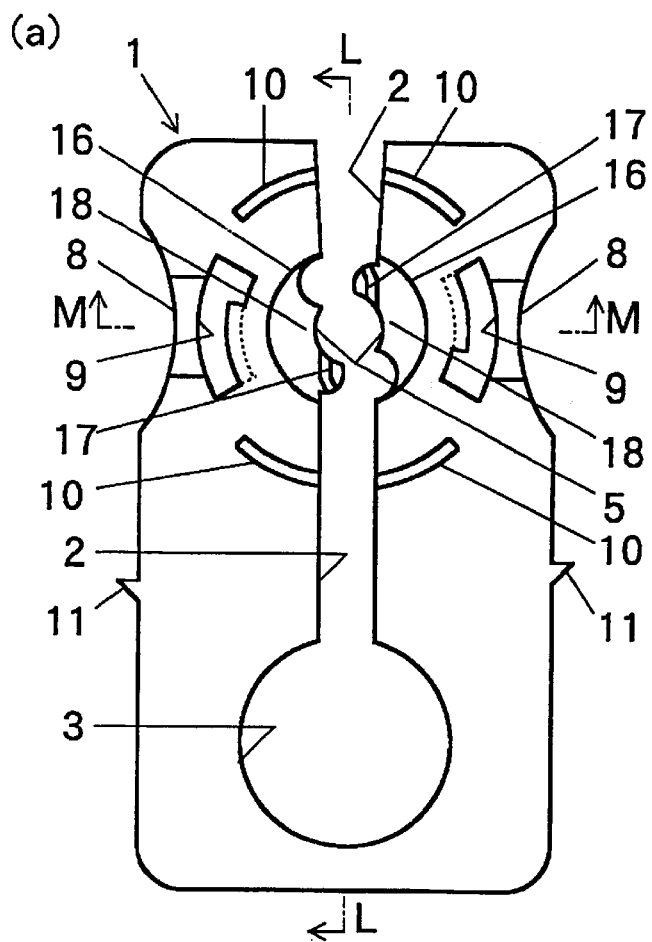
FIG. 7(a) is a plan view.
Figure 7B:
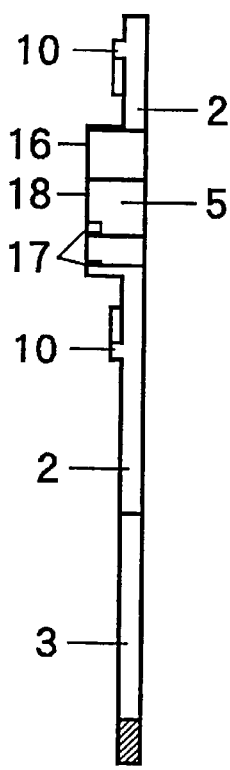
FIG. 7(b) is a cross-sectional view taken along a line L—L in FIG. 7(a) and FIG. 7(c) is a cross-sectional view taken along a line M—M in FIG. 7(a)
Figure 7C:
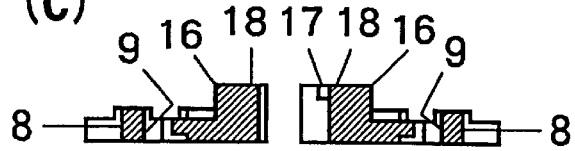

The flat mound portion 16 located in a left side portion of the base plate 1 with respect to the groove 2 (in the plan view of FIG. 7(a)) is provided with a slightly curved slit 17 in its upper surface of an arch-like projection, which is formed at a base end side of the arch-like projection so as to pass through the upper surface in a direction along the groove 2 as shown in FIG. 7. Also, the flat mound portion 16 in a right side portion of the base plate 1 is provided with a slightly curved slit 17 in its upper surface of an arch-like projection, which is formed at a top end side of the arch-like projection so as to pass through the upper surface in a direction along the groove 2. The haptics of an intraocular lens are fitted to these slits 17 which provide holding portions having a function to prevent lens rotation.

These flat mound portions 16 are formed at symmetrical positions with respect to a point on the centerline passing along the groove 2. Arch-like recesses are formed, at symmetrical positions with respect to a point in the centerline passing in a longitudinal direction in the groove 2, in an intermediate portion of the mound portions 16. The recesses are opposed to each other so that upper portions of recesses function as clamping portions 18. The pair of clamping portions 18 clamp the optical portion of the intraocular lens having the haptics which are placed on the holding portions 17 having a function to prevent lens rotation which are adjacent thereto.

The groove 2 formed in the base plate 1 is gradually broadened from a position corresponding to the lens receiving mechanism 5, 16, 17, 18 to the top end side of the base plate 1. The other features of the base plate 1 are the same as those in the first embodiment.

The soft intraocular lens container of this embodiment comprises the base plate 1 with the above-mentioned lens receiving mechanism 5, 16, 17, 18, a cover 21 which may be the same as that of the first embodiment and a prevention means for displacement 31 which may be the same as that of the first embodiment.

When the pair of grasping portions 8 of the base plate 1 are grasped, the optical portion of the soft intraocular lens clamped between the pair of clamping portions 18 is folded into two along a folding line which is the diameter of the optical lens extending along a direction of the groove 2, and the two-folded optical portion is projected upward between the clamping portions 18.

A third embodiment of the soft intraocular lens container will be described with reference to FIG. 8.

In the soft intraocular lens container having a folding function in the first embodiment, when outer sides of left and right side portions of the base plate 1 with respect to the groove 2 are compressed toward the groove 2 to bring the left and right portions close to each other, any or both of the pair of clamping portions 6 may shift in a direction of the thickness of the base plate 1. In considering the above, this embodiment of the present invention is to increase a preventive effect for displacement in the soft intraocular lens container of the first embodiment.

A base plate 41 in the third embodiment has an arch-like connecting bar 42 for preventing displacement, which projects beyond the top end of the base plate 1 and which bridges left and right side portions at the top end of the base plate 1 with respect to the groove 2 in the first embodiment, whereby an elongated circular opening 43 extending in a direction perpendicular to a longitudinal direction of the base plate is formed inside the connecting bar 42. By providing the connecting bar 42, it is unnecessary to form a portion including the guiding projections 10 formed in the top end portion of the base plate 1 in the first embodiment. The construction of the base plate 41 excluding the above-mentioned feature is the same as that of the base plate 1 in the first embodiment.

The soft intraocular lens container of the second embodiment comprises the above-mentioned base plate 41 with the connecting bar 42, the cover 2 which is the same as that of the first embodiment and the preventive means for displacement 31 which is the same as that of the first embodiment.

When both side portions (i.e., left and right sides with respect to the groove 2) of the base plate 41 are grasped from their outer side, the side portions shift toward the groove 2 along the guide plate 32 of the preventive means for displacement 31 to approach each other. Then, the arch-like connecting bar 42 is curved whereby an optical portion of a soft intraocular lens, which is held in the lens receiving mechanism and is clamped between the pair of clamping portions 6, is folded into two, and the two-folded optical portion is projected upward between the clamping portions 6.

In this embodiment, the pair of clamping portions 6 are prevented from shifting in the direction of the thickness of the base plate 41 by not only the preventive means for displacement 31 but also the connecting bar 42. The connecting bar is a constituent element of the preventive means for displacement. The other features of the second embodiment are the same as those of the first embodiment.

A fourth embodiment of the soft intraocular lens container of the present invention will be described with reference to FIG. 9.

In this embodiment, the number of parts is reduced in case that the connecting bar 42 is sufficient to perform a preventive effect for displacement in the soft intraocular lens container having a folding function in the third embodiment.

Figure 9:
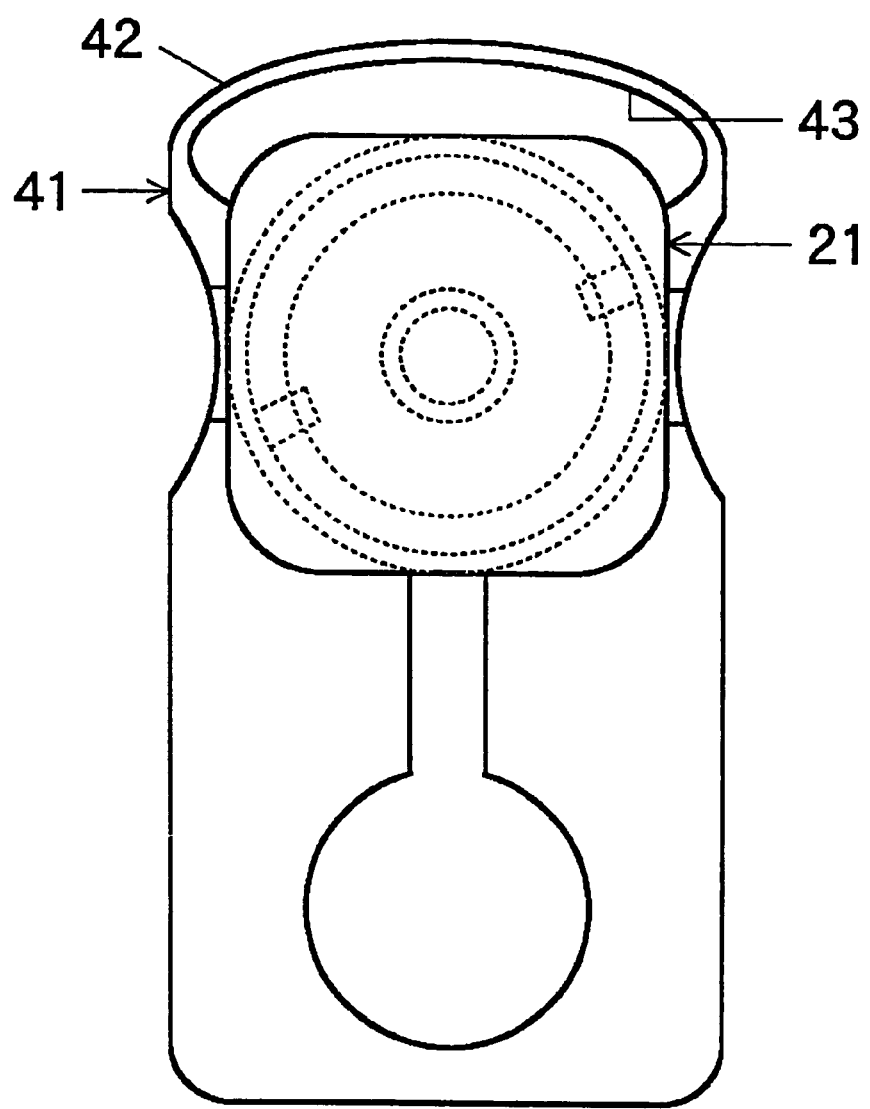
FIG. 9 is a plan view of the soft intraocular lens container having a folding function according to a fourth embodiment of the present invention.

As shown in FIG. 9, the soft intraocular lens container eliminates the preventive means for displacement 31 and the raised portions 11 of the base plate 41, which are for engaging the preventive means for displacement 31, and is constituted by only the base plate 41 with the connecting bar 42 and the cover 21. The other features are the same as those of the third embodiment.

In the soft intraocular lens according to the first aspect of the present invention, when a soft intraocular lens received in the container is folded, (1) the cover is removed from the base plate, and (2) the both side portions of the base plate are clamped so that the both side portions are pressed toward the groove whereby the optical portion of the soft intraocular lens clamped between the clamping portions formed at both sides of the groove is folded into two.

The two-folded soft intraocular lens is picked up with forceps for inserting in a state of being folded, the two-folded soft intraocular lens picked up with the forceps for inserting is inserted into the crystal lens capsule of an eye through an incision.

Accordingly, in comparison with the second conventional case, many operations and much labor are not required in folding the soft intraocular lens received in the container.

Further, since the soft intraocular lens is picked up with the forceps for inserting from the container, the number of times of delivery is small. Accordingly, a much time and much labor are not required for the delivery unlike the first conventional case. There is a little possibility that the intraocular lens is stained, damaged or dropped during the delivery. Further, expensive forceps for taking out and forceps for folding are unnecessary.

Further, since the container has such construction that the haptics of the soft intraocular lens are placed on the holding portions of the base plate, and the optical portion of the soft intraocular lens is clamped between the clamping portions of the base plate, the position of the optical portion which is pressed and folded can be a position near an upper edge of the clamping portions. Accordingly, it is unnecessary to bring the forceps for inserting to a deep position in the narrow space between the clamping portions when the optical portion folded between the clamping portions is picked up with the forceps for inserting. Thus, the picking operation can be easy.

According to the second aspect of the present invention, two-folded soft intraocular lens is projected from the space between the opposing clamping portions. Accordingly, it is easy to pick up the soft intraocular lens with the forceps for inserting.

According to the third aspect of the present invention, the lens surface of the optical portion of the soft intraocular lens, which is received in the lens receiving mechanism, does not contact the lens receiving mechanism. Accordingly, the lens surface of the optical portion does not stick to the lens receiving mechanism even when the optical portion has some stickiness.

According to the fourth aspect of the present invention, when the both side portions of the base plate is clamped so that the side portions are pressed toward the groove, the preventive means for displacement prevents either or both of the clamping portions formed at opposite positions with respect to the groove are shifted in a direction of the thickness of the base plate. Accordingly, the intraocular lens can correctly be folded into two.

According to the fifth aspect of the present invention, the preventive means for displacement provides an excellent prevention effect for displacement since the both side portions of the base plate are deflected toward the groove along the guide plate.

Obviously, numerous modifications and variations of the present invention are possible in light of the above teachings. It is therefore to be understood that within the scope of the appended claims, the invention may be practiced otherwise than as specifically described herein.

The entire disclosure of Japanese Patent Application JP11-350545 filed on Dec. 9, 1999 including specification, claims, drawings and summary are incorporated herein by reference in its entirety.

What is claimed is:

1. A soft intraocular lens container having a folding function which comprises:

a base plate having a groove, a lens receiving mechanism formed in the base plate, said lens receiving mechanism comprising a pair of holding portions, each formed at each side portion of the groove, which are adapted to receive haptics of a soft intraocular lens, and clamping portions, each formed on each of the holding portions, which clamp an optical portion of the soft intraocular lens having said haptics to be put on said holding portions, wherein said base plate is capable of folding the optical portion of the soft intraocular lens held between said clamping portions into two when both-sides of the base plate are clamped so that the base plate is pressed toward the groove, and a cover having a plurality of bayonet pawls projecting toward a rear surface side of the cover, said bayonet pawls being capable of engaging with bayonet openings formed in the base plate at both side portions with respect to the groove whereby the cover covers the soft intraocular lens received in the lens receiving mechanism and is fixed to the both side portions of the base plate with respect to the groove.

2. The soft intraocular lens container having a folding function according to claim 1, wherein the lens receiving mechanism is adapted to raise the optical portion of the soft intraocular lens from a space between the clamping portions when the optical portion is folded into two.

3. The soft intraocular lens container having a folding function according to claim 1, wherein the lens receiving mechanism is adapted so that a lens surface of the optical portion does not contact the lens receiving mechanism when the optical portion is received in the lens receiving mechanism.

4. The soft intraocular lens container having a folding function according to claim 1, which further comprises preventive means for displacement which prevents any of the clamping portions from shifting in a direction of the thickness of the base plate when the both sides of the base plate are clamped so that the base plate is pressed toward the groove.

5. The soft intraocular lens container having a folding function according to claim 4, wherein the preventive means for displacement has a guide plate extending along a rear surface of the base plate, and the guide plate is provided at its base end side with an insertion portion for receiving a base end side of the base plate.

* * * * *